United States Patent
Groepper et al.

(10) Patent No.: US 10,173,044 B2
(45) Date of Patent: Jan. 8, 2019

(54) LOCKING TAPER FLUID CONNECTION INTERFACES

(71) Applicant: TA Instruments—Waters L.L.C., Milford, MA (US)

(72) Inventors: Charles Groepper, Waconia, MN (US); Aaron M. Owens, Plymouth, MN (US); Thomas M. Hays, Blaine, MN (US)

(73) Assignee: TA INSTRUMENTS—WATERS L.L.C., Milford, MA (US)

( * ) Notice: Subject to any disclaimer, the term of this patent is extended or adjusted under 35 U.S.C. 154(b) by 588 days.

(21) Appl. No.: 14/856,792

(22) Filed: Sep. 17, 2015

(65) Prior Publication Data

US 2016/0084414 A1    Mar. 24, 2016

Related U.S. Application Data

(60) Provisional application No. 62/052,864, filed on Sep. 19, 2014.

(51) Int. Cl.
*A61M 39/10* (2006.01)
*F16L 37/00* (2006.01)

(52) U.S. Cl.
CPC .......... *A61M 39/10* (2013.01); *F16L 37/008* (2013.01); *A61M 2039/1033* (2013.01); *A61M 2039/1038* (2013.01)

(58) Field of Classification Search
CPC .. A61M 2039/1033; A61M 2039/1038; A61M 2039/1055; A61M 39/12; A61M 39/10; F16L 37/008; F16L 21/08; F16L 37/12
See application file for complete search history.

(56) References Cited

U.S. PATENT DOCUMENTS

| | | | | |
|---|---|---|---|---|
| 3,057,350 A | * | 10/1962 | Cowley | A61M 39/223 137/607 |
| 3,394,954 A | * | 7/1968 | Sarns | A61M 39/10 285/319 |
| 4,675,007 A | * | 6/1987 | Terry | A61M 39/12 285/283 |
| 4,745,950 A | * | 5/1988 | Mathieu | A61M 39/26 137/798 |

(Continued)

FOREIGN PATENT DOCUMENTS

WO    WO 2014164971 A1 * 10/2014 ........ A61M 39/1011

*Primary Examiner* — David Bochna
(74) *Attorney, Agent, or Firm* — Womble Bond Dickinson (US) LLP; Deborah M. Vernon; Heath T. Misley

(57) ABSTRACT

This document provides fluid handling components. For example, this document relates to taper interface connections such as, but not limited to, luer taper interface connections used to couple fluid handling components in a medical or laboratory setting. In some embodiments, the threaded connection on the male portion of the taper interface is comprised of one or two opposing tabs, rather than a 360° collar like conventional luer lock fittings. As such, the taper interface components provided herein are readily manufacturable with a lower cost than conventional fittings that have a collar. In some embodiments, the taper interface components provided herein are configured for coupling by way of a quick connection technique.

7 Claims, 6 Drawing Sheets

(56) References Cited

U.S. PATENT DOCUMENTS

| | | | | |
|---|---|---|---|---|
| 5,071,413 A * | 12/1991 | Utterberg | ............. | A61M 39/10 604/411 |
| 5,603,706 A * | 2/1997 | Wyatt | ................... | A61M 39/10 137/223 |
| 5,688,254 A * | 11/1997 | Lopez | ............... | A61M 39/1011 604/529 |
| 5,797,897 A * | 8/1998 | Jepson | ............... | A61M 39/1011 604/239 |
| 5,810,792 A * | 9/1998 | Fangrow, Jr. | ...... | A61M 39/1011 285/319 |
| 5,839,715 A * | 11/1998 | Leinsing | ............ | A61M 39/1011 251/149.1 |
| 5,899,888 A * | 5/1999 | Jepson | ............... | A61M 39/1011 604/201 |
| 6,488,666 B1 * | 12/2002 | Geist | ................... | A61M 5/3213 604/192 |
| 6,726,672 B1 * | 4/2004 | Hanly | ............... | A61M 39/1011 215/247 |
| 7,927,312 B2 * | 4/2011 | Sogaro | ................. | A61M 5/178 604/187 |
| 2017/0173321 A1 * | 6/2017 | Davis | ................... | A61M 39/10 |

\* cited by examiner

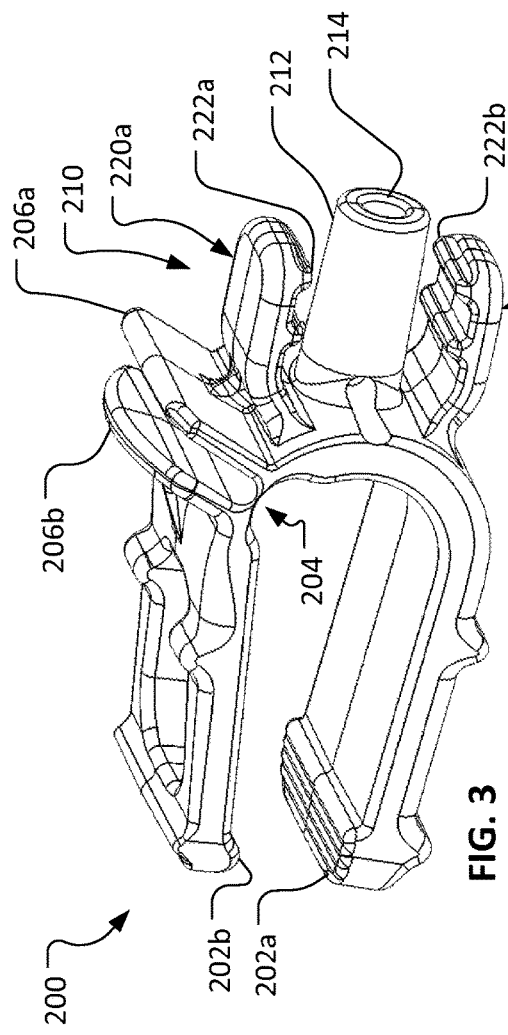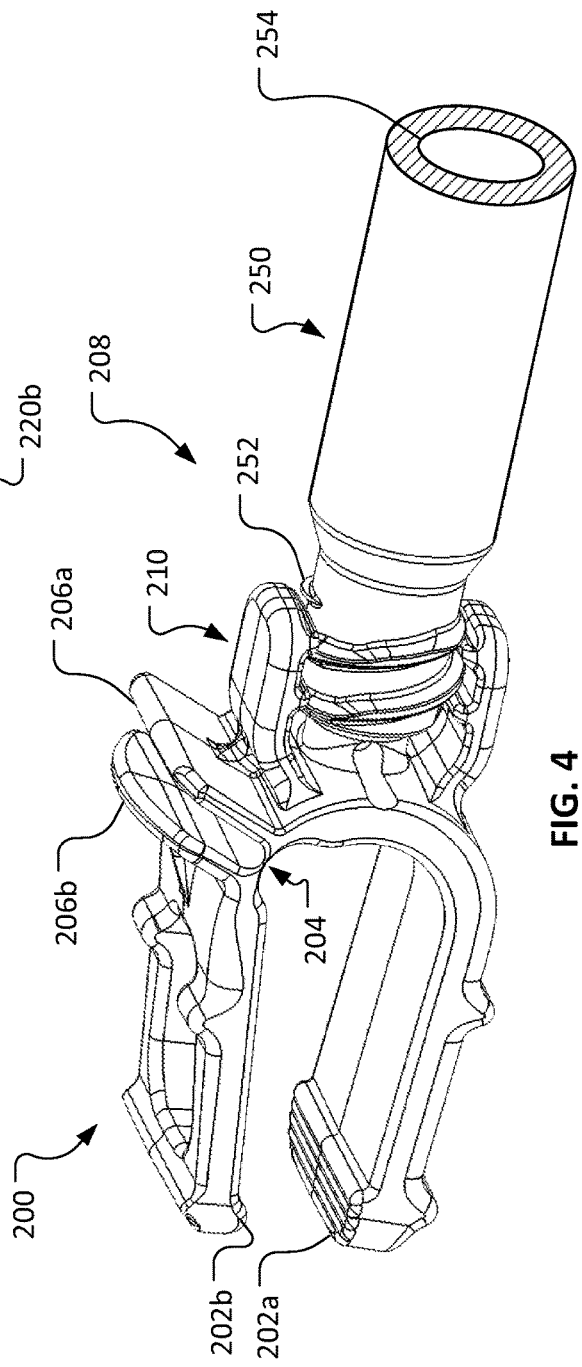

LOCKING TAPER FLUID CONNECTION INTERFACES

RELATED APPLICATIONS

This application claims priority to and the benefit of U.S. Application No. 62/052,864, entitled "Locking Taper Fluid Connection Interfaces" filed on Sep. 19, 2014, the contents of which are incorporated by reference in their entirety herein.

TECHNICAL FIELD

This document relates to fluid handling component interfaces. For example, this document relates to taper interface connections such as, but not limited to, luer taper interface connections used to couple fluid handling components in a medical or laboratory setting.

BACKGROUND INFORMATION

Fluid systems commonly include components such as tubing, pumps, reservoirs, heat exchangers, sensors, filters, valves, manifolds, bulkheads, and the like. Such components can be connected together to define a fluid flow path. Some fluid systems are open systems, meaning that the fluid flows through the network once and then exits the network. Other fluid systems are closed systems, meaning that the fluid recirculates within the network of components. Fluids are caused to flow in the fluid system using fluid pressure differentials. In some cases, a pump is used to create a pressure differential that causes the fluid to flow within the fluid system. In some cases, a vacuum source or gravity is used to create a pressure differential that causes the fluid to flow within the fluid system. In some cases, a combination of such techniques is used to create a pressure differential that causes the fluid to flow within the fluid system.

Some fluid system connections are intended to be removable leak-free connections that are also resistant to disconnection when subjected to an axial force. For example, a luer taper is a standardized type of fluid fitting used for making leak-free connections between a male-taper fitting and a mating female part on medical and laboratory instruments. Features of luer taper connectors are defined in the ISO 594 and EN 1707 standards. In general, there are two varieties of luer taper connections: a luer lock fitting and a luer slip fitting. Luer lock fittings are securely joined by means of external threads on the female fitting which screw into internal threads in a sleeve on the male fitting. Luer slip fittings simply conform to luer taper dimensions and are pressed together and held by friction (they have no threads). Luer taper components are manufactured from either metal or plastic and are available from many companies worldwide.

SUMMARY

This document provides fluid handling component interfaces. For example, this document provides taper interface connections such as, but not limited to, luer taper interface connections used to couple fluid handling components in a medical or laboratory setting.

In one implementation, a taper interface connection system includes a male component and a female component that is releasably coupleable with the male component. The male component includes a first tab with a first thread portion and a tapered male body having an axial male component lumen therethrough. The tapered male body is spaced apart from the first tab by a distance. The female component includes an external thread that meshes with the first thread portion when the male component and the female component are coupled (and additionally in the process of being coupled). The female component defines a female component lumen and a tapered female space that tightly receives the tapered male body when the male component and the female component are coupled. The male component lumen and the female component lumen are in essentially leak-proof fluid communication when the male component and the female component are coupled. That is, when coupled the male component lumen and the female component lumen provide fluid communication therebetween that is substantially leak-proof (e.g., leak-tight coupling).

Such a taper interface connection system may optionally include one or more of the following features. The male component and the female component may both comprise moldable materials. The male component and the female component may both comprise metal materials. The tapered male body and the tapered female space may be compliant with a recognized standard for luer fittings. The male component may further comprise a second tab with a second thread portion. The second tab may be disposed in relation to the first tab such that the second thread portion faces the first thread portion at about a 180° orientation. The second tab may be spaced apart from the tapered male body by the distance. The second thread portion may mesh with the external thread when the male component and the female component are coupled and in the process of being coupled.

In another implementation, a taper interface connection system includes a male component and a female component that is coupleable with the male component. The male component includes a first tab with a first teeth portion, a second tab with a second teeth portion, and a tapered male body having an axial male component lumen therethrough. The second tab is disposed in relation to the first tab such that the second teeth portion faces the first teeth portion. The tapered male body is disposed between the first tab and the second tab, and spaced apart from the first tab and the second tab by equal distances. The female component includes one or more annular rings that are spaced apart from each other such that the one or more annular rings are configured to engage with the first teeth portion and the second teeth portion in a complementary arrangement when the male component and the female component are coupled. The female component defines a female component lumen and a tapered female space that tightly receives the tapered male body when the male component and the female component are coupled. The male component lumen and the female component lumen are in essentially leak-proof fluid communication when the male component and the female component are coupled. That is, when coupled the male component lumen and the female component lumen provide fluid communication therebetween that is substantially leak-proof (e.g., leak-tight connection/coupling).

Such a taper interface connection system may optionally include one or more of the following features. The second tab may be disposed in relation to the first tab such that the second teeth portion faces the first teeth portion at about a 180° orientation. The male component and the female component may both comprise moldable materials. The tapered male body and the tapered female space may be compliant with a recognized standard for luer fittings. The male component and the female component may be coupled by applying a compressive force to move the one or more annular rings past at least a portion of the first teeth portion and past at least a portion of the second teeth portion. The compressive force may cause at least some of the one or more annular rings to deflect. The compressive force may cause at least some portions of the first teeth portion and at least some portions of the second teeth portion to deflect. The compressive force may cause the first tab, the second tab, or both the first tab and the second tab to deflect.

In another implementation, a taper interface connection system includes a male component and a female component that is coupleable with the male component. The male component includes a first tab with a first thread portion, a second tab with a second thread portion, and a tapered male body having an axial male component lumen therethrough. The second tab is disposed in relation to the first tab such that the second thread portion faces the first thread portion. The tapered male body is disposed between the first tab and the second tab and spaced apart from the first tab and the second tab by equal distances. The female component includes a first external thread portion and a second external thread portion that is separate from the first external thread portion. The first external thread portion and the second external thread portion each individually mesh with either the first thread portion or the second thread portion when the male component and the female component are coupled (and, in certain embodiments, in the process of being coupled). The female component defines a female component lumen and a tapered female space that tightly receives the tapered male body when the male component and the female component are coupled. The male component lumen and the female component lumen are in essentially leak-proof fluid communication when the male component and the female component are coupled. That is, when coupled the male component lumen and the female component lumen provide fluid communication therebetween that is substantially leak-proof (e.g., leak-tight coupling)

Such a taper interface connection system may optionally include one or more of the following features. The male component and the female component may both comprise moldable materials. The male component and the female component may both comprise metals. The tapered male body and the tapered female space may be compliant with a recognized standard for luer fittings. The tapered male body, the tapered female space, the first thread portion, the second thread portion, and the external thread may all be compliant with a recognized standard for luer lock fittings. The male component and the female component may be coupleable by rotating the male component by about 90° in relation to the female component.

In another implementation, a mechanical clamping device includes a clamp portion and a male taper interface portion extending from the clamp portion. The clamp portion includes at least two contact faces and a load element configured to cause the two contact faces to apply a clamping force to the sample when loaded into the mechanical clamping device. Each contact face is configured to contact a sample when loaded into the mechanical clamping device. A first of the contact faces is configured to travel in response to an applied force. The male taper interface portion includes a first tab with a first thread portion, a second tab with a second thread portion, and a tapered male body having an axial male component lumen therethrough. The tapered male body disposed between the first tab and the second tab and spaced apart from the first tab and the second tab by equal distances. The second tab being disposed in relation to the first tab such that the second thread portion faces the first thread portion.

Such a mechanical clamping device may optionally include one or more of the following features. The clamp portion and the male taper interface portion may both comprise moldable materials. The tapered male body may be compliant with a recognized standard for luer fittings. The mechanical clamping device may further comprise a female taper interface portion that is releasably coupleable with the male taper interface portion. The female taper interface portion may comprise an external thread that meshes with the first thread portion and the second thread portion when the male taper interface portion and the female taper interface portion are coupled (and, in some embodiments, in the process of being coupled). The female taper interface portion may define a female component lumen and a tapered female space that tightly receives the tapered male body when the male taper interface portion and the female taper interface portion are coupled. The male component lumen and the female component lumen may be in essentially leak-proof fluid communication when the male taper interface portion and the female taper interface portion are coupled. That is, when coupled the male component lumen and the female component lumen provide fluid communication therebetween that is substantially leak-proof (e.g., leak-tight coupling).

Particular embodiments of the subject matter described in this document can be implemented to realize one or more of the following advantages. First, the taper interfaces provided herein allow for low cost manufacture. That is the case at least because such taper interfaces can be injection molded, and the molded part can be removed from the mold without requiring rotation of the mold or part, or a collapsing mold. Consequently, a less complex injection molding system, or a less labor-intensive process, can be used to mold the taper interfaces provided herein in comparison to conventional lock fittings that have a threaded collar. Therefore, the costs to mold the taper interfaces provided herein can be lower than conventional lock fittings. Such lower costs may also facilitate smaller production runs, which can be advantageous in some circumstances. Second, the taper interfaces provided herein are more convenient to thoroughly clean and decontaminate in comparison to conventional lock fittings that have a threaded collar. That is the case because the taper interfaces provided herein do not have the enclosed spaces that are difficult to clean like conventional lock fittings that have a threaded collar. Such an advantage is particularly advantageous for fluid handling components used in a medical or laboratory setting. Third, in some embodiments the taper interfaces provided herein are quicker and more convenient to couple and decouple than conventional lock fittings that have a threaded collar. Fourth, in some embodiments the taper interfaces provided herein are more compact than conventional luer lock fittings. Therefore, devices that incorporate the taper interfaces provided herein can be made advantageously smaller than devices using conventional lock fittings that have a threaded collar.

Unless otherwise defined, all technical and scientific terms used herein have the same meaning as commonly understood by one of ordinary skill in the art to which this invention pertains. While various methods and materials are described in this application, other similar or equivalent methods and materials are possible and can be used in place or partial substitution for the disclosed methods and materials. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 3 is a perspective view of an example device that is configured to utilize the taper interface of FIG. 1.

FIG. 4 is a perspective view showing the device of FIG. 3 showing the taper interface on the device coupled with a mating component.

Like reference numbers represent corresponding parts throughout.

DETAILED DESCRIPTION

This document provides fluid handling component interfaces. For example, this document provides taper interface connections such as, but not limited to, luer taper interface connections used to couple fluid handling components in a medical or laboratory setting. As described further below, in some embodiments the threaded connection on the male portion of the taper interface is comprised of one tab or two opposing tabs, rather than a 360° collar like conventional lock fittings. As such, the taper interface components provided herein are readily manufacturable at a lower unit cost than conventional lock fittings that have a threaded collar. Further, in some embodiments the taper interface components provided herein are configured for coupling by way of a quick connection technique.

Figure 1:
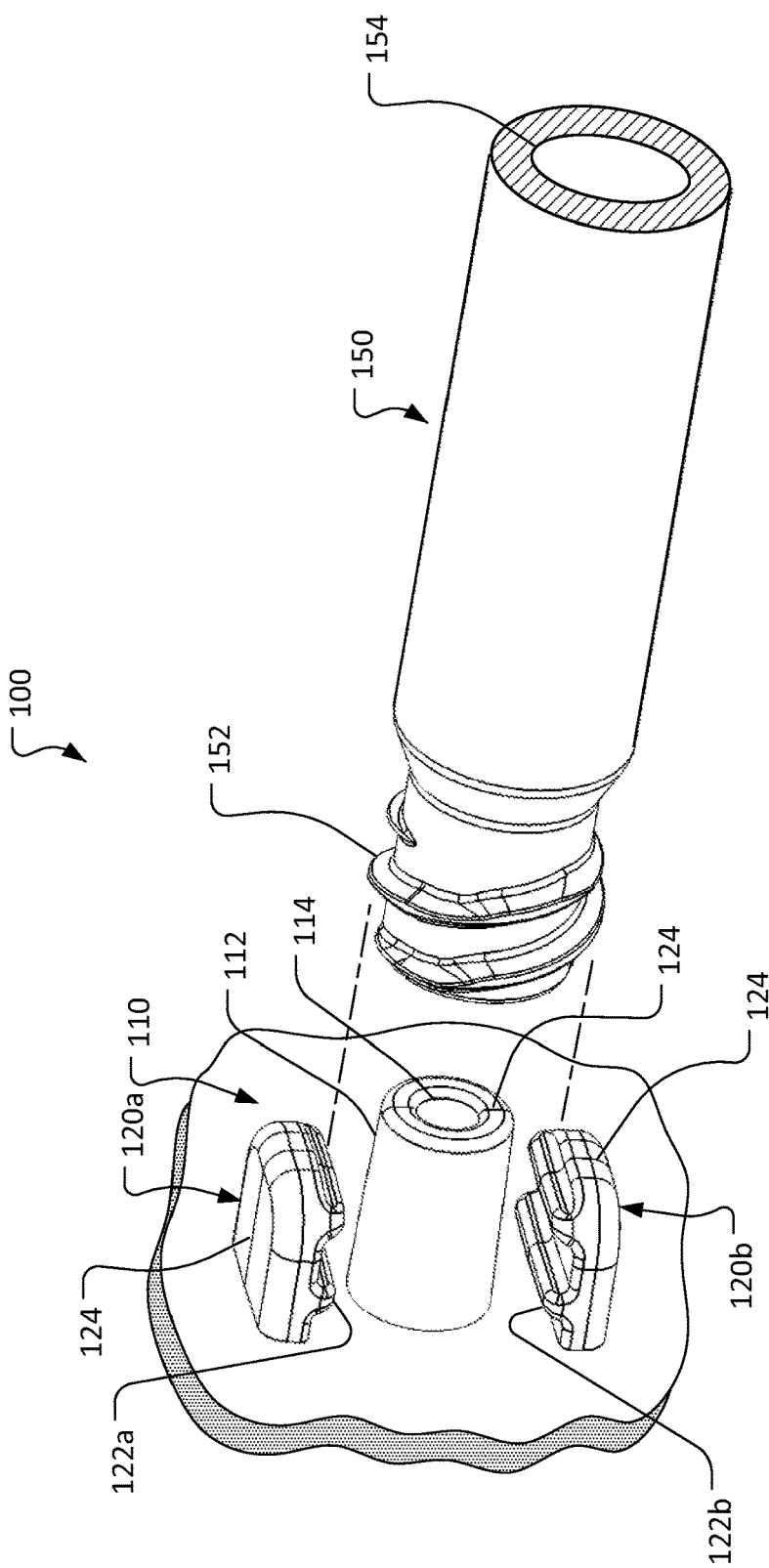
FIG. 1 is an exploded perspective view of an example taper interface in accordance with some embodiments.

Referring to FIG. 1, an example taper interface 100 includes a male component 110 and a female component 150. In this example implementation, the male component 110 is represented by a bulkhead-style connection, and the female component 150 is represented by a tube. However, it should be understood that such representations are merely examples, and that the taper interface 100 is not limited to such contexts. Rather, the taper interface 100 can be advantageously implemented in a wide variety of different contexts. For example, the male component 110 and/or the female component 150 can be implemented as a part of components such as, but not limited to, a syringe, a stopcock, a Y-connector, a T-connector, an elbow fitting, a catheter, a solution bag, a coupling, a two-way valve, a three-way valve, a hose assembly, a filter, a cap, a bubble trap, an adapter, an introducer, an IV line, a PICC line, an infusion catheter, medical devices, laboratory instruments, fluid handling systems, and the like, and combinations thereof. The components of the taper interface 100 can be made from a variety of known materials including, but not limited to, thermoplastics, metals, ceramics, polymers, synthetic materials, natural materials, and the like, and combinations thereof.

In the depicted embodiment, the male component 110 includes a male taper portion 112, a first tab 120a, and a second tab 120b. In alternate embodiments, only a single tab is included. The male taper portion 112 is disposed substantially equidistantly between the first tab 120a and the second tab 120b. The first tab 120a and the second tab 120b are disposed generally opposite from each other in relation to the centered male taper portion 112. In some embodiments, the first tab 120a and the second tab 120b are disposed about 180° opposite from each other in relation to the centered male taper portion 112. When used in the context of the opposing tabs of the taper interfaces provided herein, "about 180°" can be understood to mean in the range of about 160° to about 200°.

The physical structure and dimensions of the male taper portion 112 can be selected in accordance with the design requirements of a particular implementation. In some embodiments of the taper interfaces provided herein, the physical structure and dimensions of the male taper portion 112 are selected in accordance with the governing standards for luer tapers. However, in some embodiments of the taper interfaces provided herein the physical structure and dimensions of the male taper portion 112, while tapered, are not necessarily compliant with the governing standards for luer tapers. It should be understood that the male and female tapers of all taper interfaces provided herein can be either a luer taper or a non-luer taper, and that both scenarios are within the scope of this disclosure. The male taper portion 112 has a male component lumen 114 that can facilitate fluid flow through the male taper portion 112.

The first tab 120a includes threads 122a. The second tab 120b includes threads 122b. As will be described further below, the threads 122a and 122b are configured to function cooperatively as internal threads for connecting the female component 150 to the male component 110. That is, the threads 122a and 122b facilitate a threaded connection between the male component 110 and the female component 150. In some embodiments, the threads 122a and 122b can be of a design that is selected in accordance with the governing standards for luer lock fittings, but it is not required that the threads 122a and 122b conform to the luer lock standards in all embodiments. In some embodiments, various other designs for the threads 122a and 122b can be selected, as long as the threads 122a and 122b are complementary with the threads of a mating component.

A typical male luer lock fitting includes an internally threaded collar instead of the first tab 120a and the second tab 120b. Such collars are cylindrical rings that fully surround the male taper portion 112 (in a coaxial relationship), and that have threads on the inner diameter of the ring. Because of such collars, the typical male lock fitting with a collar requires more complex molding equipment than what is required to mold the taper interface 100.

In some embodiments, the male taper portion 112 can be advantageously molded by relatively standard injection molding equipment, and the molded part can be removed from the mold without requiring rotation of the mold or the molded male taper portion 112. For example, an injection mold can be designed having a mold parting line 124 located on the first tab 120a, the male taper portion 112, and the second tab 120b as shown. To mold a typical male luer lock fitting requires either a side action mold with rotation capability, a collapsible mold, or a manual pick out process. Owing to the design of the tabs 120a and 120b of the taper interface 100, a less complex injection molding system, or a less labor-intensive process, can be used to mold the taper interface 100 (and other embodiments provided herein) in comparison to conventional lock fittings that have a threaded collar. In result, the costs to mold the taper interfaces provided herein can be lower than conventional lock fittings. Such lower costs may also facilitate smaller production runs, which can be advantageous in some circumstances.

In the depicted embodiment, the female component 150 includes external threads 152, a female component lumen 154, and an internal taper portion (not visible). One of ordinary skill in the art will understand that the internal taper portion of the female component 150 slidably engages with the male taper portion 112 to create a close fit that tends to be leak proof in some implementations. The female component lumen 154 can facilitate fluid flow through the female component 150 (either towards or away from the end on which the external threads 152 are disposed). In some embodiments, the external threads 152 can be of a design that is selected in accordance with the governing standards for luer lock fittings. In some embodiments, other designs for the external threads 152 can be selected, as long as the external threads 152 are complementary with the threads of a mating component (such as the first tab 120a and the second tab 120b).

Figure 2:
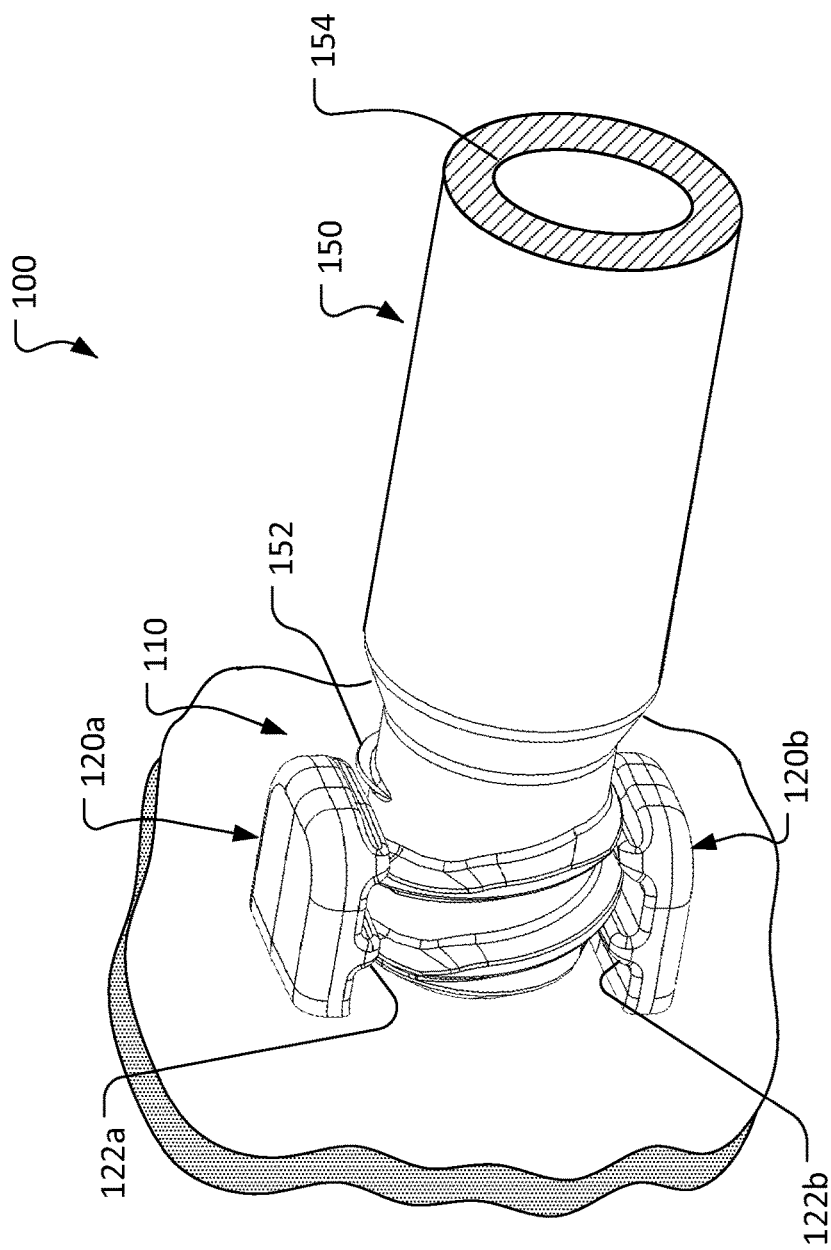
FIG. 2 is a perspective view showing the taper interface of FIG. 1 in a coupled configuration.

Referring also to FIG. 2, the male component 110 and the female component 150 can be releasably coupled by engaging the internal threads 122a and 122b of the male component 110 with the external threads 152 of the female component 150. By tightening the engagement of the threads 122a and 122b with the threads 152 the male component 110 and the female component 150 are drawn closer together, and the male taper portion 112 is closely engaged with the internal taper portion of the female component 150. Such an arrangement can provide a leak-proof seal in accordance with the governing standards for luer tapers.

While the depicted embodiment includes two tabs (the first tab 120a and the second tab 120b), it is not a requirement that all embodiments of the taper interfaces provided herein include two tabs. In some embodiments, a single tab is included. In some such embodiments, the single tab can be generally configured and orientated like either of the first tab 120a or the second tab 120b.

With the male component 110 and the female component 150 releasably coupled, the female component lumen 154 is in fluid communication with the male component lumen 114. Consequently, when the male component 110 and the female component 150 are coupled, fluids can flow through lumens 114 and 154 to facilitate fluid transmission between the male component 110 and the female component 150 in a substantially leak-proof manner.

Referring to FIGS. 3 and 4, in one example, a taper interface 208 can be implemented on an example clamping device 200. In the depicted embodiment, the clamp 200 includes two contact faces 202a and 202b (or "contact faces 202a-b" collectively) configured to, when moved towards each other, apply a clamping force to a sample (e.g., a biologic material, a synthetic material, a combination of a biologic material and a synthetic material, native tissue, processed tissue, cell-seeded biomaterial scaffolds, tissue-engineered constructs, medical devices, acellular biomaterials, scaffolds, and the like) held by the clamp 200.

In some implementations, the clamp 200 may be used to hold a sample so that one or more tests may be run on the sample. For example, a user may expose the sample to a particular gaseous environment, a growth medium, lighting conditions, chemical, biological, and/or mechanical manipulations such as repeated tension tests. For example, the clamp 200 may have been sterilized before installation, and may require contact with only sterile forceps to load the sample. In another example, the clamp 200 may be used for a different purpose. For example, the clamp 200 may hold a sample in preparation of a medical procedure, as part of a manufacturing process, and so on. In some embodiments, a load element such as an elastic member is included to provide force that causes the two contact faces 202a and 202b to apply a clamping force to the sample when loaded into the clamping device 200.

The clamp 200 includes a hinge 204 that the contact face 202b rotates about in order to make contact with either the other contact face 202a or a sample loaded between the two contact faces 202a-b. To move the contact face 202b, the clamp 200 includes two spreader arms 206a and 206b that are manipulatable to spread the contact faces 202a-b apart. For example, a human operator may use their fingers or a tool such as forceps to manipulate the spreader arms 206a-b.

The hinge 204 may be a living hinge. In some embodiments, other types of hinges can be used. In general, living hinges include hinges that are, or contain, a thin, flexible element made of the same material as the pieces it connects. In the case of the clamp 200, the clamp 200 can be made of a plastic that is flexible at the living hinge 204 but effectively rigid at thicker elements of the clamp 200. Because of the nature of the plastic, the clamp 200 may be opened to a greater extent (that is the contact faces 202a-b may be moved farther apart) by applying a compressive force to the two spreader arms 206a-b. The clamp 200 may then return to the shape as shown when that compressive force is removed, or the contact faces 202a-b may be in contact with each other.

In the depicted embodiment, the clamp 200 includes an integral male component 210 of the taper interface 208 in accordance with embodiments provided herein. The male component 210 includes a male taper portion 212, a first tab 220a, and a second tab 220b. The male taper portion 212 is disposed equidistantly between the first tab 220a and the second tab 220b. The first tab 220a and the second tab 220b are disposed generally opposite of each other in relation to the centered male taper portion 212. In some embodiments, the first tab 220a and the second tab 220b are disposed at about 180° opposite from each other in relation to the centered male taper portion 212. In some embodiments, the physical structure and dimensions of the male taper portion 212 are selected in accordance with the governing standards for luer tapers. However, in some embodiments of the taper interfaces provided herein the physical structure and dimensions of the male taper portion 212, while tapered, are not necessarily compliant with the governing standards for luer tapers. It should be understood that the male and female tapers of all taper interfaces provided herein can be either a luer taper or a non-luer taper, and that both scenarios are within the scope of this disclosure. The male taper portion 212 has a male component lumen 214 that, in some embodiments, can facilitate fluid flow through the male taper portion 212.

The first tab 220a includes threads 222a. The second tab 220b includes threads 222b. As will be described further below, the threads 222a and 222b are configured to function cooperatively as internal threads for connecting a female component 250 to the male component 210. That is, the threads 222a and 222b facilitate a threaded connection between the male component 210 and the female component 250. In some embodiments, the threads 222a and 222b can be of a design that is selected in accordance with the governing standards for luer lock fittings. In some embodiments, other designs for the threads 222a and 222b can be selected, as long as the threads 222a and 222b are complementary with the threads of a mating component (e.g., female component 250).

In the depicted embodiment, the female component 250 includes external threads 252, a female component lumen 254, and an internal taper portion (not visible). One of ordinary skill in the art will understand that the internal taper portion of the female component 250 slidably engages with the male taper portion 212 to create a close fit that tends to be leak proof in some implementations. In some embodiments, the female component lumen 254 can facilitate fluid flow through the female component 250 (either towards or away from the end on which the external threads 252 are disposed). In some embodiments, the external threads 252 can be of a design that is selected in accordance with the governing standards for luer lock fittings. In some embodiments, other designs for the external threads 252 can be selected, as long as the external threads 252 are complementary with the threads of a mating component (e.g., male component 210).

Figure 5:
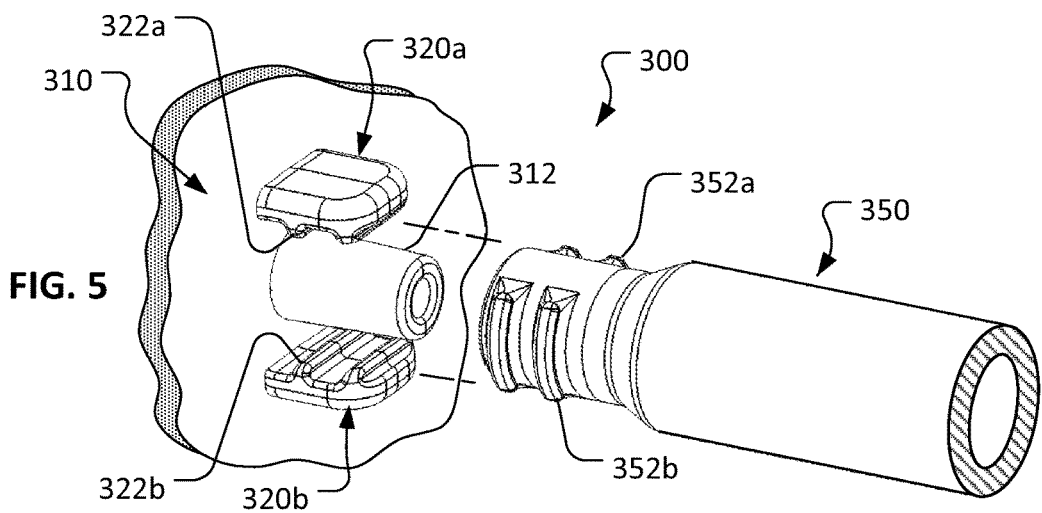
FIG. 5 is an exploded perspective view of another example taper interface in accordance with some embodiments.
Figure 6:
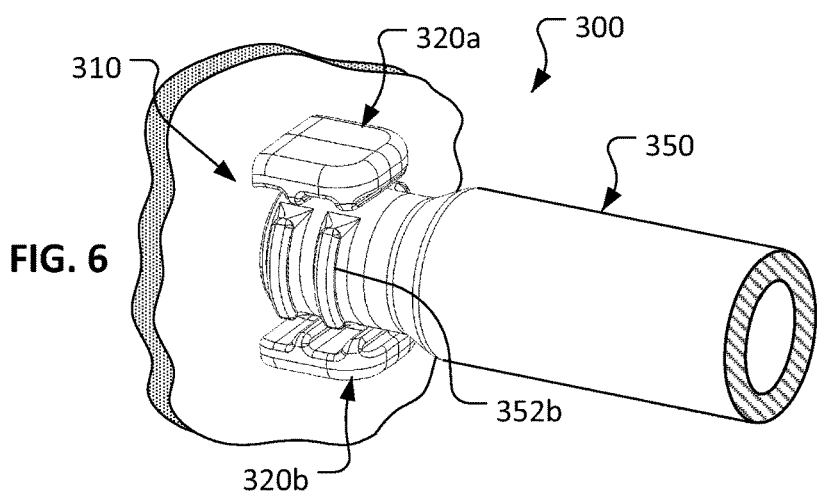
FIG. 6 shows the taper interface of FIG. 5 with the male and female components engaged but not interlocked with each other.
Figure 7:
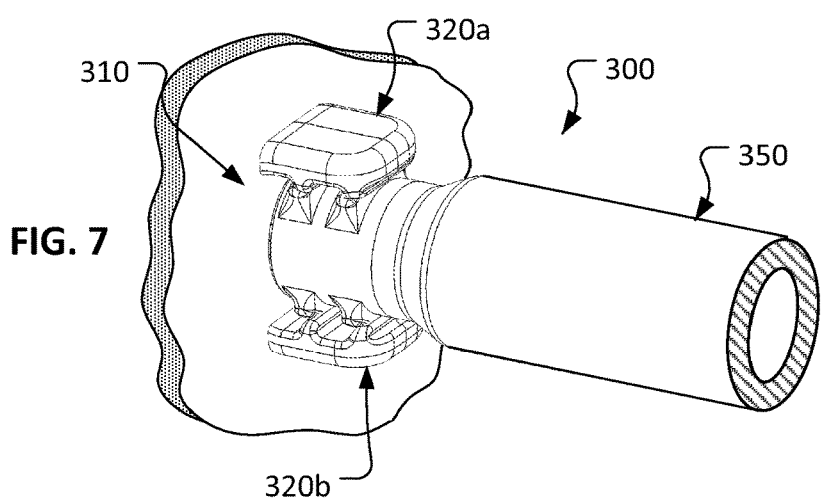
FIG. 7 shows the taper interface of FIG. 5 with the male and female components in a coupled and interlocked configuration.

Referring to FIGS. 5-7, another example embodiment of taper interface 300 includes a male component 310 and a female component 350. In this example implementation, the male component 310 is represented by a bulkhead-style connection, and the female component 350 is represented by a tube. However, it should be understood that such representations are merely examples, and that the taper interface 300 is not limited to such contexts. Rather, the taper interface 300 can be advantageously implemented in a wide variety of different contexts such as, but not limited to, those contexts described above in reference to taper interface 100.

The taper interface 300 shares many of the features, characteristics, and benefits of the taper interface 100 as described above. However, the taper interface 300 is specially configured for coupling by way of a quick ¼-turn connection technique.

To facilitate the ¼-turn connection technique, the female component 350 includes two thread portions: threads 352a and threads 352b. As depicted in FIGS. 5 and 6 collectively, the threads 352a and 352b are configured in relation to the threads 322a and 322b of the tabs 320a and 320b so that the taper 312 of the male component 310 and the taper of the female component 350 can be slidably engaged without rotation therebetween. Thereafter, as depicted in FIGS. 6 and 7 collectively, the male component 310 and the female component 350 can be rotated about 90° in relation to each other to tightly interlock the male component 310 and the female component 350. The ¼-turn connection technique reduces the need for rotation of the male component 310 and/or the female component 350 to interlock them. Therefore, the taper interface 300 provides a very convenient taper interface.

Figure 8:
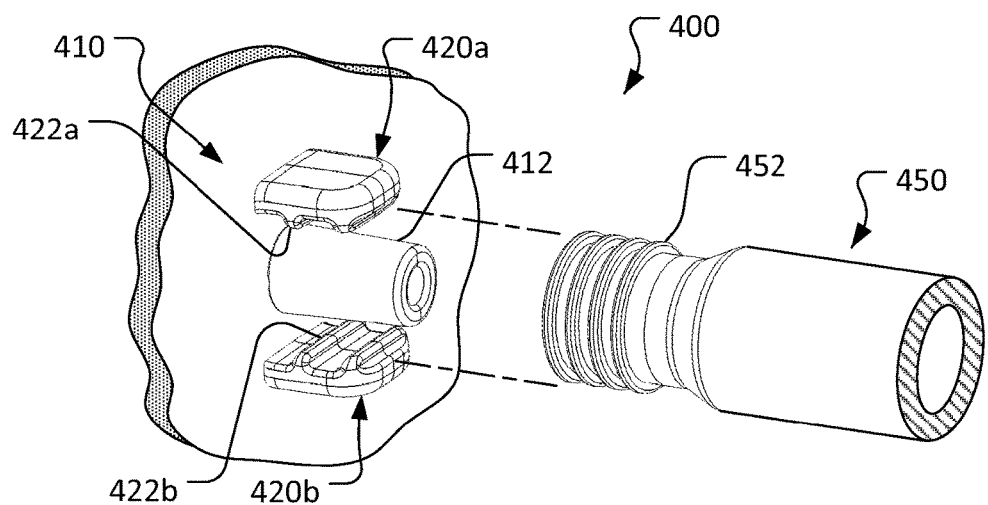
FIG. 8 is an exploded perspective view of another example taper interface in accordance with some embodiments.
Figure 9:
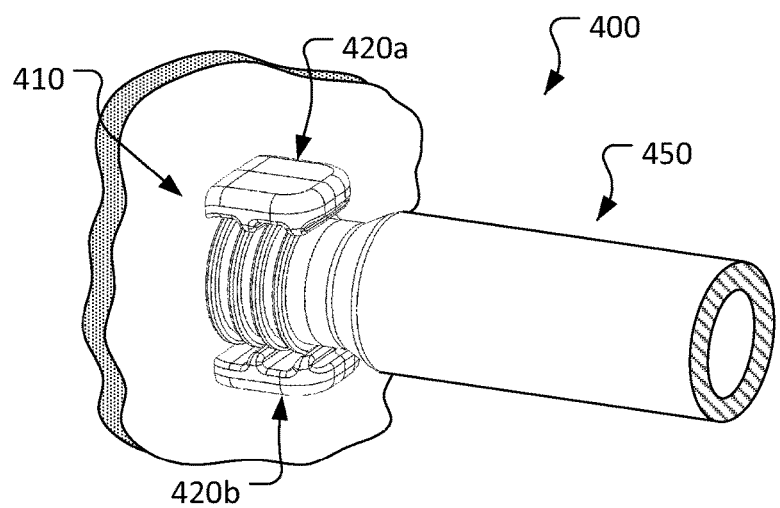
FIG. 9 shows the taper interface of FIG. 8 with the male and female components in a coupled and interlocked configuration.

Referring to FIGS. 8 and 9, another example embodiment of taper interface 400 includes a male component 410 and a female component 450. In this example implementation, the male component 410 is represented by a bulkhead-style connection, and the female component 450 is represented by a tube. However, it should be understood that such representations are merely examples, and that the taper interface 400 is not limited to such contexts. Rather, the taper interface 400 can be advantageously implemented in a wide variety of different contexts such as, but not limited to, those contexts described above in reference to taper interface 100.

The taper interface 400 shares many of the features, characteristics, and benefits of the taper interface 100 as described above. However, the taper interface 400 is specially configured for coupling by way of a quick push-on connection technique.

To facilitate the push-on connection technique of taper interface 400, the tabs 420a and 420b include one or more teeth 422a and 422b respectively. In addition, the female component 450 includes one or more annular ridges 452. The teeth 422a and 422b are configured in relation to the annular ridges 452 so that the taper 412 of the male component 410 and the taper of the female component 450 can be slidably engaged and interlocked without rotation therebetween. That is, the male component 410 and the female component 450 can be simply pushed onto each other to engage and interlock them. The push-on connection technique eliminates the need for rotation of the male component 410 and/or the female component 450 to interlock them. Therefore, the taper interface 400 provides a very convenient taper interface.

An interference fit exists between the one or more teeth 422a and 422b and the one or more annular ridges 452. Therefore, as the male component 410 and the female component 450 are compressively forced into engagement with each other, some relative deflection between the one or more teeth 422a and 422b in relation to the one or more annular ridges 452 is necessary. In some embodiments, the annular ridges 452 are more flexible than the teeth 422a and 422b, and therefore as the male component 410 and the female component 450 are pushed into engagement with each other the annular ridges 452 temporarily resiliently compress to pass over the teeth 422a and 422b. In some embodiments, the teeth 422a and 422b are more flexible than the annular ridges 452, and therefore as the male component 410 and the female component 450 are pushed into engagement with each other the teeth 422a and 422b temporarily resiliently compress to pass over the annular ridges 452. In some embodiments, as the male component 410 and the female component 450 are pushed into engagement with each other, the teeth 422a and 422b and the annular ridges 452 temporarily resiliently compress to pass over each other. In some embodiments, one or both of the tabs 420a and 420b temporarily resiliently deflect outwardly (radially away from the taper 412) to allow the one or more teeth 422a and 422b to pass over the one or more annular ridges 452.

After the male component 410 and the female component 450 are compressively forced onto each other, the interference fit between the one or more teeth 422a and 422b and the one or more annular ridges 452 creates a releasable interlock between the male component 410 and the female component 450. To disconnect the male component 410 and the female component 450, a tensile force can be applied therebetween. A tensile force that is sufficient to overcome the interference fit between the one or more teeth 422a and 422b and the one or more annular ridges 452 will be able to disconnect the male component 410 and the female component 450. Therefore, in some embodiments the push-on taper interface 400 is capable of multiple engagement and disengagement cycles.

Figure 10:
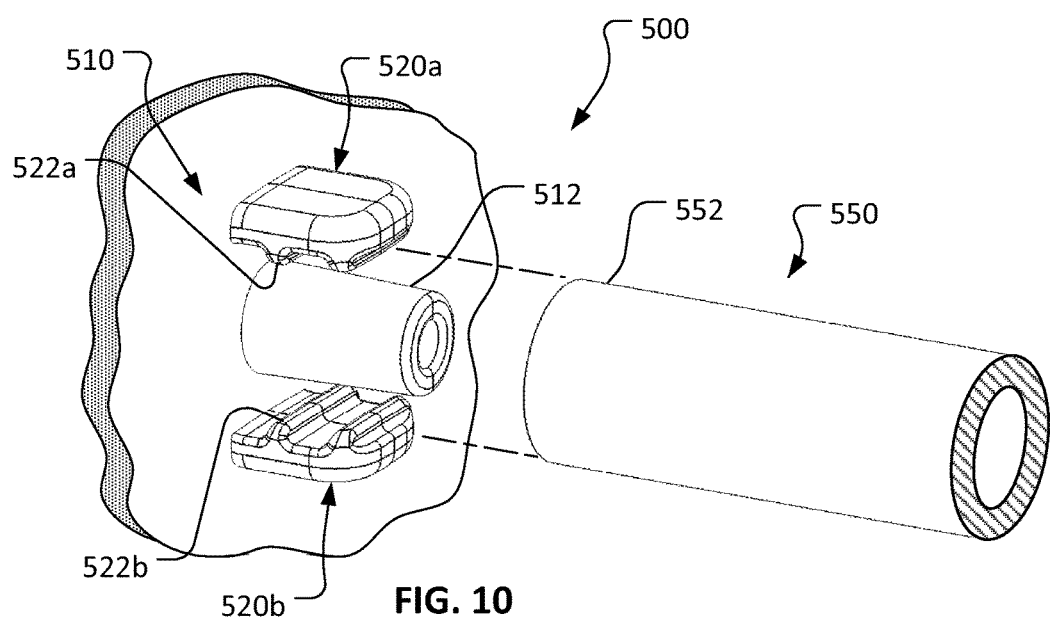
FIG. 10 is an exploded perspective view of another example taper interface in accordance with some embodiments.
Figure 11:
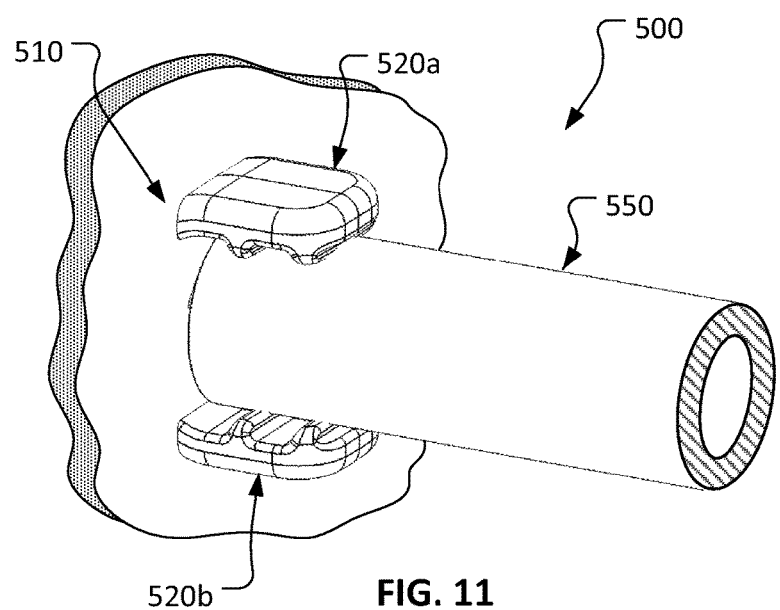
FIG. 11 shows the taper interface of FIG. 10 with the male and female components in a coupled and interlocked configuration.

Referring to FIGS. 10 and 11, another example embodiment of taper interface 500 includes a male component 510 and a female component 550. In this example implementation, the male component 510 is represented by a bulkhead-style connection, and the female component 550 is represented by a tube. However, it should be understood that such representations are merely examples, and that the taper interface 500 is not limited to such contexts. Rather, the taper interface 500 can be advantageously implemented in a wide variety of different contexts such as, but not limited to, those contexts described above in reference to taper interface 100.

The taper interface 500 shares many of the features, characteristics, and benefits of the taper interface 100 as described above. However, the taper interface 500 is specially configured for coupling by way of a quick push-on connection technique.

To facilitate the push-on connection technique of taper interface 500, the tabs 520a and 520b include one or more teeth 522a and 522b respectively. The teeth 522a and 522b are configured in relation to the outer diameter 552 of the female component 550 so that the taper 512 of the male component 510 and the taper of the female component 550 can be slidably engaged and interlocked without rotation therebetween. That is, the teeth 522a and 522b compressively bite on the outer diameter 552 of the female component 550. The compressive bite provided by the teeth 522a and 522b on the outer diameter 552 resiliently retains the male component 510 and the female component 550 in the engaged position (as shown in FIG. 11) during use of the taper interface 500. Therefore, the male component 510 and the female component 550 can be simply pushed onto each other to engage and interlock them. The push-on connection technique eliminates the need for rotation of the male component 510 and/or the female component 550 to interlock them. Therefore, the taper interface 500 provides a very convenient taper interface.

An interference fit exists between the one or more teeth 522a and 522b and the outer diameter 552 of the female component 550. Therefore, as the male component 510 and the female component 550 are compressively forced into engagement with each other, some relative deflection between the one or more teeth 522a and 522b in relation to the outer diameter 552 of the female component 550 is necessary. In some embodiments, the outer diameter 552 of the female component 550 is more flexible or compressible than the teeth 522a and 522b, and therefore as the male component 510 and the female component 550 are pushed into engagement with each other the outer diameter 552 temporarily resiliently deflects to pass over the teeth 522a and 522b. In some embodiments, the teeth 522a and 522b are more flexible or compressible than the outer diameter 552 of the female component 550, and therefore as the male component 510 and the female component 550 are pushed into engagement with each other the teeth 522a and 522b temporarily resiliently compress to pass over the outer diameter 552. In some embodiments, as the male component 510 and the female component 550 are pushed into engagement with each other, the teeth 522a and 522b and the outer diameter 552 of the female component 550 temporarily resiliently compress to pass over each other. In some embodiments, one or both of the tabs 520a and 520b temporarily resiliently deflect outwardly (radially away from the taper 512) to allow the one or more teeth 522a and 522b to pass over the outer diameter 552 of the female component 550.

After the male component 510 and the female component 550 are compressively forced into engagement with each other, the interference fit between the one or more teeth 522a and 522b and the outer diameter 552 creates a releasable interlock between the male component 510 and the female component 550. To disconnect the male component 510 and the female component 550, a tensile force can be applied therebetween. A tensile force that is sufficient to overcome the compressive bite of the one or more teeth 522a and 522b on the outer diameter 552 will be able to disconnect the male component 510 and the female component 550. Therefore, in some embodiments the push-on taper interface 500 is capable of multiple engagement and disengagement cycles.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. It should be understood that the features described in the context of a particular embodiment can be combined with one or more features that are described in the context of one or more other embodiments, and that all such resulting hybrid designs are within the scope of this disclosure.

What is claimed is:

1. A taper interface connection system comprising:
   a male component comprising:
   a first tab with a first thread portion;
   a second tab with a second thread portion, the second tab being disposed in relation to the first tab such that the second thread portion faces the first thread portion; and
   a tapered male body having an axial male component lumen therethrough, the tapered male body disposed between the first tab and the second tab and spaced apart from the first tab and the second tab by equal distances; and a female component that is releasably coupleable with the male component, the female component comprising a first external thread portion and a second external thread portion that is separate from the first external thread portion, wherein the first external thread portion and the second external thread portion are located on opposing outer portions of the female component and each individually mesh with either the first thread portion or the second thread portion when the male component and the female component are coupled, the female component defining a female component lumen and a tapered female space that tightly receives the tapered male body when the male component and the female component are coupled, wherein the male component lumen and the female component lumen are in fluid communication and provide a substantially leak-proof connection when the male component and the female component are coupled.

2. The taper interface connection system of claim 1, wherein the male component and the female component both comprise moldable materials.

3. The taper interface connection system of claim 1, wherein the male component and the female component both comprise metals.

4. The taper interface connection system of claim 1, wherein the tapered male body and the tapered female space are compliant with a recognized standard for luer fittings.

5. The taper interface connection system of claim 1, wherein the tapered male body, the tapered female space, the first thread portion, the second thread portion, and the external thread are all compliant with a recognized standard for luer lock fittings.

6. The taper interface connection system of claim 1, wherein the male component and the female component are coupleable by rotating the male component by about 90° in relation to the female component.

7. A mechanical clamping device comprising:
a clamp portion comprising:
   at least two contact faces, a first of the contact faces configured to travel in response to an applied force, each contact face configured to contact a sample when loaded into the mechanical clamping device; and
   a load element configured to cause the two contact faces to apply a clamping force to the sample when loaded into the mechanical clamping device; and
a male taper interface portion extending from the clamp portion and comprising:
   a first tab with a first thread portion;
   a second tab with a second thread portion, the second tab being disposed in relation to the first tab such that the second thread portion faces the first thread portion;
   a tapered male body having an axial male component lumen therethrough, the tapered male body disposed between the first tab and the second tab and spaced apart from the first tab and the second tab by equal distances; and
   a female component that is releasably coupleable with the tapered male body, the female component comprising a first external thread portion and a second external thread portion that is separate from the first external thread portion, wherein the first external thread portion the second external thread portion are located on opposing outer portions of the female component and each individually mesh with either the first thread portion or the second thread portion when the tapered male body and the female component are coupled.

* * * * *